(12) United States Patent
Inagawa et al.

(10) Patent No.: US 6,526,315 B1
(45) Date of Patent: Feb. 25, 2003

(54) PORTABLE BIOELECTRICAL IMPEDANCE MEASURING INSTRUMENT

(75) Inventors: Hideaki Inagawa, Tokyo (JP); Yusuke Ito, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/631,626

(22) Filed: Aug. 4, 2000

Related U.S. Application Data

(60) Provisional application No. 60/189,985, filed on Mar. 17, 2000.

(51) Int. Cl.$^7$ .................................. A61B 5/05
(52) U.S. Cl. ...................................... 600/547
(58) Field of Search ........................ 600/547

(56) References Cited

U.S. PATENT DOCUMENTS

| | | | |
|---|---|---|---|
| 4,008,712 A | | 2/1977 | Nyboer |
| 6,188,925 B1 | * | 2/2001 | Kawanishi et al. .......... 600/547 |
| 6,243,651 B1 | * | 6/2001 | Masuo .......................... 702/19 |
| 6,292,690 B1 | * | 9/2001 | Petrucelli et al. ........... 600/547 |
| 6,327,495 B1 | * | 12/2001 | Iwabuchi et al. ........... 600/547 |

FOREIGN PATENT DOCUMENTS

| EP | 0 926 488 A2 | 6/1999 |
|---|---|---|
| JP | 11-70092 | 3/1999 |

* cited by examiner

*Primary Examiner*—Robert L. Nasser
*Assistant Examiner*—Patricia Mallari
(74) *Attorney, Agent, or Firm*—McDermott, Will & Emery

(57) ABSTRACT

A multi-function portable bioelectrical impedance measuring instrument is provided that is easily held in the hand, and has its electrodes and its controls arranged to be easily manipulated. Embodiments include an instrument wherein a pair of electrodes is arranged on the back of a main body of the instrument such that they are both contacted by a user's palm when the main body is held in the palm of the hand. Another pair of electrodes, a set of operating switches, and a display are located on the face (i.e., the front) of the main body such that two fingers of the other hand of the user can touch the electrodes simultaneously and operate the instrument to obtain a body fat occupancy ratio and/or pulse rate based on the impedance measured by the electrodes. A photoelectric detector is also provided on the face of the main body to produce a signal to provide a blood pressure reading or pulse rate. Since the electrodes can be firmly held in contact with the user's skin due to their ergonomic arrangement, the instrument is easily operated and produces accurate monitoring of body fat occupancy ratio, pulse rate, blood pressure, and the like.

44 Claims, 5 Drawing Sheets

PORTABLE BIOELECTRICAL IMPEDANCE MEASURING INSTRUMENT

RELATED APPLICATIONS

This application claims priority from U.S. Provisional Patent Application No. 60/189,985 filed Mar. 17, 2000, which is incorporated herein by reference.

FIELD OF THE INVENTION

The present invention relates to a portable bioelectrical impedance measuring instrument for measuring an electric impedance using four electrodes for measuring body fat occupancy ratio, blood pressure, pulse rate and the like.

BACKGROUND ART

A conventional portable body fat monitor is disclosed in Japanese Utility Model Publication No. 5-2164. This body fat monitor has a display and an operator unit formed on the face of a main body. Four measurement electrodes are formed in pairs on the back of the main body. Each pair of measurement electrodes is touched with one finger of the right or left hand.

Namco Ltd. has put a body fat monitor, which looks like a pocket game machine, on the market. This monitor has one electrode formed on both sides of a main body.

Yamato Scale Co., Ltd. has marketed portable body fat monitors named "Poke-navi" and "Poke-mini" having electrodes formed on the upper left and right parts of the face and back of a main body.

Japanese Unexamined Patent Application Publication No. 11-700092 discloses a portable body fat monitor having electrodes formed on the top and bottom of a card.

Casio Computer Co., Ltd. is selling a blood pressure monitor that has two electrodes and a photoelectric sensor formed on a main body shaped like an elliptic cylinder.

Additionally, an electronic pulsimeter having a photoelectric sensor formed on a main body shaped like an elliptic cylinder has made its debut.

The body fat monitor disclosed in Japanese Utility Model Publication No. 5-2164 suffers from poor maneuverability. This is because the main body must be turned inside out in order to touch the electrodes with fingers for the purpose of measuring a body fat occupancy ratio, and then turned back after completion of measurement. Moreover, although the four measurement electrodes are formed on the back, each pair of electrodes must be touched with one finger of the right or left hand. The spacing between each pair of electrodes is therefore so narrow that precision measurement is compromised.

The body fat monitor marketed by Namco Ltd. suffers from the same drawback, i.e., lack of precision, as the body fat monitor described in Utility Model Publication 5-2164. The monitor is small enough to be enclosed in one hand. When the monitor is held with both hands for measurement, the majorities of the fingers of the right and left hands touch each other, leading to a considerably large error in measurement.

The body fat monitor sold by Yamato Scale Co., Ltd. also suffers from poor maneuverability. An operator switch must be pressed while the electrodes are touched with the fingers, so the fingers must be largely separated from one another or the main body must be held in an awkward manner.

The monitor disclosed in the Japanese Unexamined Patent Application Publication No. 11-70092 has the electrodes distributed to the four corners of the monitor. Consequently, a lengthy connection cord is needed. The monitor is therefore susceptible to extraneous electric noises or the like.

The Casio blood pressure monitor and the electronic pulsimeter each have only a single function.

There exists a need for a multi-function portable bioelectrical impedance measuring instrument that provides accurate measurements and is easy to operate.

SUMMARY OF THE INVENTION

An advantage of the present invention is a portable impedance measuring instrument for monitoring body fat, blood pressure, and pulse rate, the instrument having electrodes arranged so that the instrument is easily operated by a user, thereby facilitating accurate measurements.

Additional advantages and other features of the present invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other advantages are achieved in part by a portable bioelectrical impedance measuring instrument comprising a main body, a first pair of electrodes on a face of the main body, a second pair of electrodes on a back side of the main body opposite the face, and an operator unit and display unit on the face. The instrument is small enough to be held in the palm of one hand, while the electrodes on the face of the main body are touched with fingers of the other hand. Thus, a user can hold the instrument easily and in a stable manner, leading to increased measurement precision.

Another aspect of the present invention is a portable bioelectrical impedance measuring instrument comprising a main body, a first pair of electrodes on a face of the main body, a second pair of electrodes on opposing sides of the main body, and an operator unit and display on the face. The instrument is sized to be held in the palm of one hand, while the electrodes on the face of the main body are touched with fingers of the other hand. Thus, a user can hold the instrument easily and in a stable manner, leading to increased measurement precision.

A still further aspect of the present invention is a portable bioelectrical impedance measuring instrument comprising a main body, two pairs of electrodes on a pair of opposing sides of the main body, and an operator unit and display on a face of the main body. The instrument is sized to be held in the palm of one hand. A bioelectrical impedance is accurately measured by the four electrodes to monitor body fat occupancy ratio, pulse rate, blood pressure or the like while the instrument is held in one hand.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Conventional portable bioelectrical impedance measuring instruments have their components arranged such that the instruments are difficult for the user to manipulate, resulting in inaccurate measurements, and/or do not provide a large range of functions. The present invention addresses and solves these problems stemming from conventional non-ergonomic, non-versatile portable bioelectrical instruments.

According to the present invention, a portable bioelectrical impedance measuring instrument is provided that is easily held in one hand, and has its four electrodes and its controls arranged to be easily manipulated. In one embodiment of the present invention, a pair of electrodes is arranged on the back of a main body of the instrument such that they are both contacted by a user's palm when the main body is held in the palm of the hand. Another pair of electrodes, a set of operating switches, and a display are located on the face (i.e., the front) of the main body such that two fingers of the other hand of the user can touch the electrodes simultaneously and operate the instrument to obtain a body fat occupancy ratio and/or pulse rate based on the impedance measured by the electrodes. A photoelectric detector is optionally provided on the face of the main body to produce a signal to provide a blood pressure reading or pulse rate. Thus, the present invention provides an easily operated instrument that produces accurate readings, since the electrodes can be firmly held in contact with the user's skin due to their ergonomic arrangement. Moreover, the present invention provides a multi-functional instrument for monitoring body fat occupancy ratio, pulse rate, blood pressure, and the like.

Figure 1:
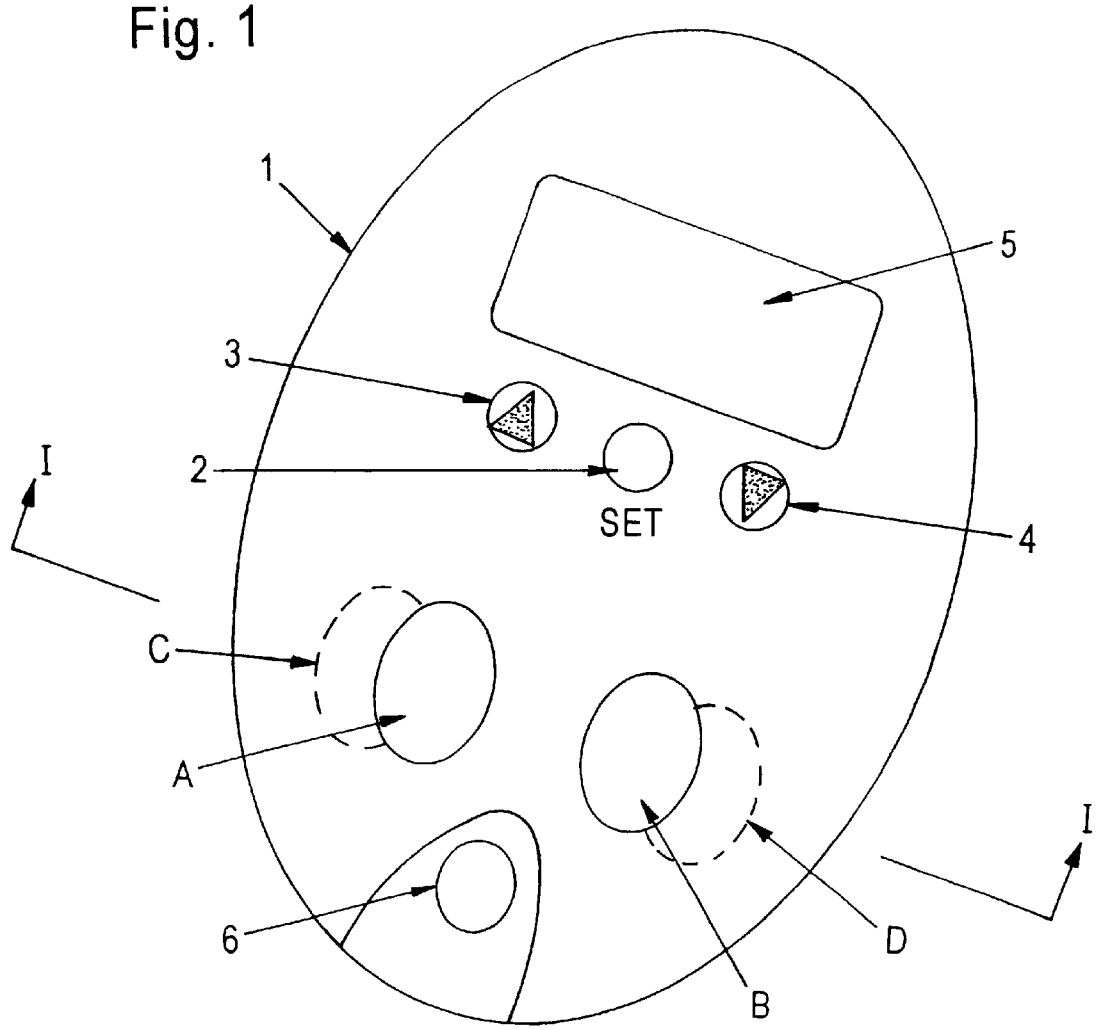
FIG. 1 illustrates a portable bioelectrical impedance measuring instrument in accordance with a first embodiment of the present invention.

Embodiments of the present invention will now be described with reference to the drawings. Referring to FIG. 1, a Set switch 2, such as a push button, used to switch the power supply of the measuring instrument and select a mode, is located in the center of the face of a main body 1 of a portable bioelectrical impedance measuring instrument. An Up switch 3 and a Down switch 4, such as push buttons, are located on the left and right sides of the Set switch 2.

When the Set switch 2 is operated once, the power supply is turned on. The measuring instrument is placed in a body fat measurement mode in which data stored in a memory is displayed. When the Set switch 2 is operated again, the body fat measurement mode is switched to a re-measurement mode in which a body fat occupancy ratio is measured using the data stored in the memory. When the Set switch 2 is operated again, the re-measurement mode is switched to a new measurement mode in which a body fat occupancy ratio is measured anew. When the Set switch 2 is operated again, the new measurement mode is switched to a blood pressure measurement mode in which a blood pressure is measured. When the set switch 2 is operated again, the blood pressure measurement mode is switched to a pulse measurement mode in which a pulse rate is measured. Every time the switch is operated, one mode is switched to another.

When the Up switch 3 is repeatedly turned on or held on in the new measurement mode, the value of displayed data is increased. The Down switch 4 is used to decrease the displayed data that has been increased using the Up switch 3. A display unit 5 is disposed on the face of the main body 1 in order to display data that is set or entered using the switches, the results of measurement, a guidance message for measurement, or the like.

Figure 2:
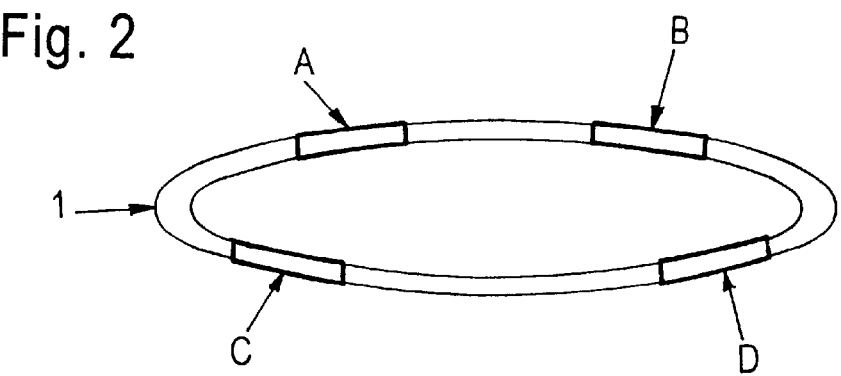
FIG. 2 is a cross sectional view taken through line I—I of the measuring instrument shown in FIG. 1.

An electrode A having an inductive metallic chip or a metallic plating is located in the lower part of the face of the main body 1. An electrode B made of the same material as the electrode A is located on the right side of the electrode A. Electrodes C and D made of the same material as the electrodes A and B are located on the back of the main body 1 and are separated from each other a bit more widely than the electrodes A and B. The main body 1 is placed in the palm of the right hand, such that the electrodes C and D are touched with the palm of the right hand. The electrodes A and B are touched with the middle finger and index finger of the left hand. The electrodes C and D are separated from each other more widely than the electrodes A and B because when the electrodes C and D are close to each other, the contact of the electrodes C and D with the palm becomes unstable because of the round shape of the palm. The fingers with which the electrodes A and B are touched are not limited to the middle and index fingers but can be any fingers. Moreover, the placement of the right hand and left hand can be reversed. FIG. 2 is a cross sectional view taken through line I—I of the measuring instrument shown in FIG. 1, showing the relative spacing of electrodes A, B, C, D.

A photoelectric sensor 6 having a light emitting device such as an LED and an optical sensor incorporated therein is located in the lower part of the main body 1.

Figure 3:
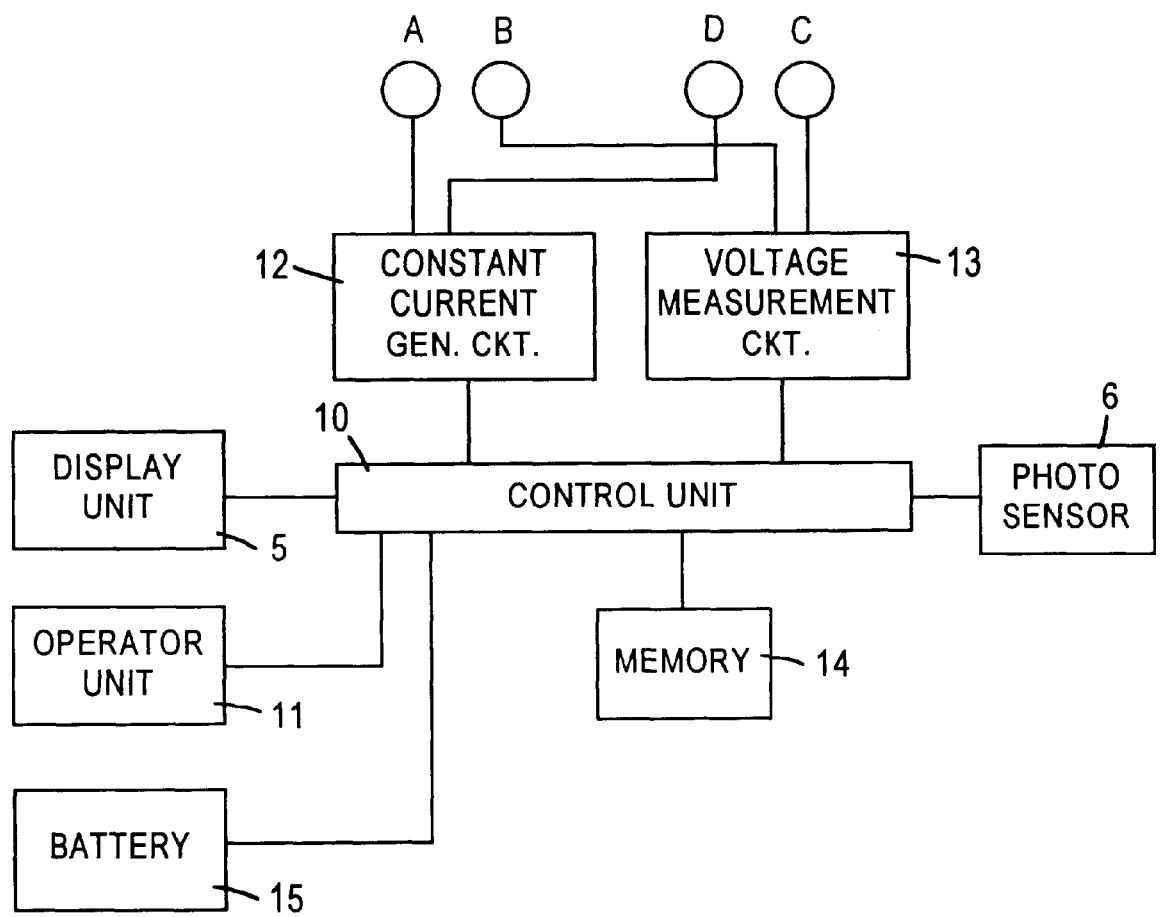
FIG. 3 schematically illustrates the electric circuitry of the measuring instrument shown in FIG. 1.

FIG. 3 shows the electric circuitry of the portable bioelectrical impedance measuring instrument shown in FIG. 1. A control unit 10 processes data sent from the operator unit 11 composed of the Set switch 2, Up switch 3, and Down switch 4. The results of arithmetic operations are displayed on the display unit 5. A constant current generation circuit 12 for supplying a constant current to the electrodes A and D is connected to the control unit 10. A voltage measurement circuit 13 for measuring the voltages at the electrodes B and C is also connected to the control circuit 10. A memory 14 for storing data read at the operator unit 11 and data indicating the results of arithmetic operations is also connected to the control unit 10. Photoelectric sensor 6 is also connected to the control unit 10.

When the Set switch 2 is turned on, electricity is supplied from a battery 15 to the components. An automatic power off timer is incorporated in the control unit 10 in order to turn off the supply of electricity.

Figure 4:
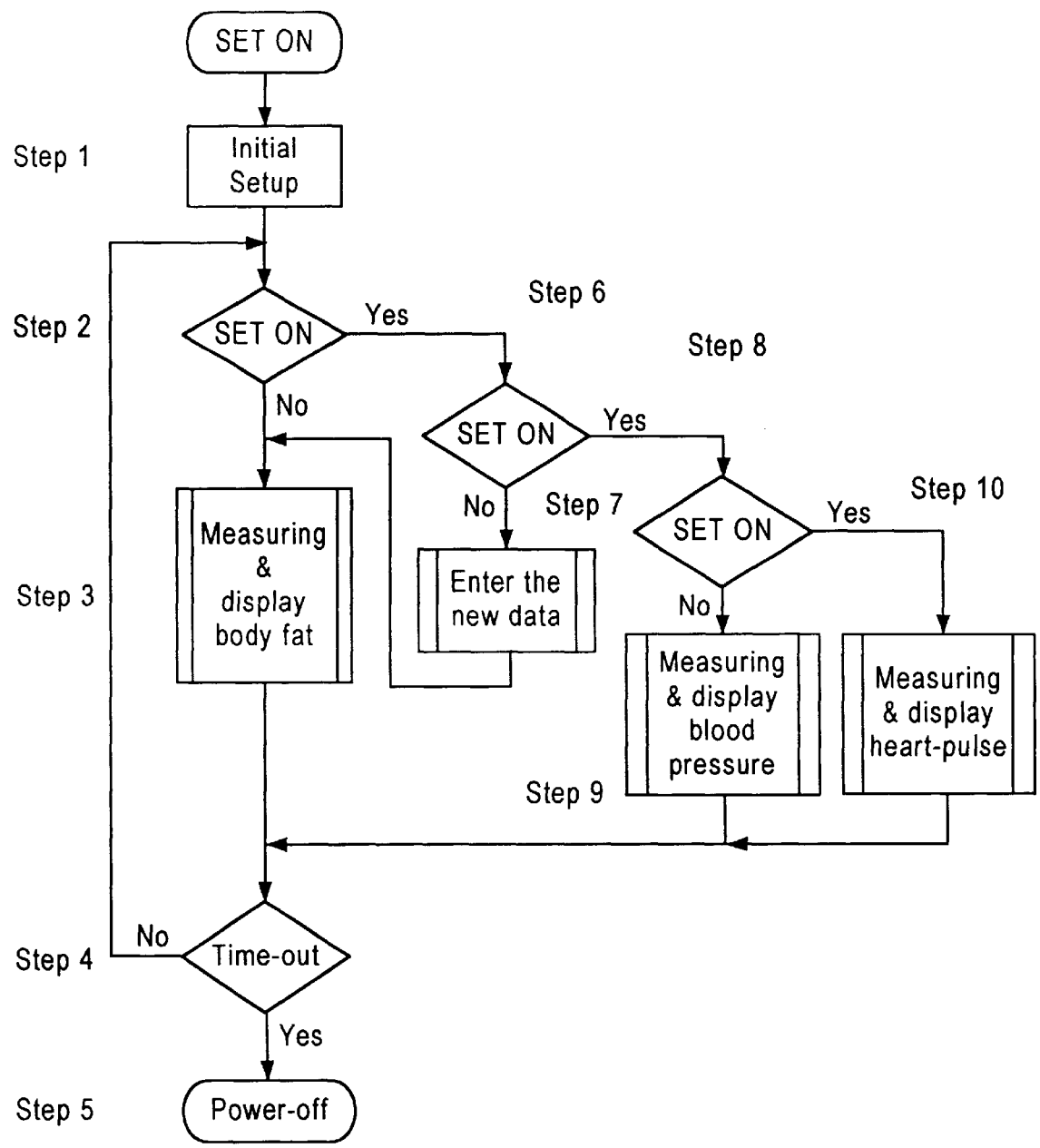
FIG. 4 is a flowchart describing actions to be performed in the measuring instrument shown in FIG. 1.

FIG. 4 is a flowchart describing actions to be performed in an embodiment of the present invention. Using the flowchart, the actions to be performed in a bioelectrical impedance measuring instrument according to the present invention will be described. First, the Set switch 2 shown in FIG. 1 is turned on. Electricity is then supplied to the circuits and control unit shown in FIG. 2 (step 1). At step 1, the display unit and circuits are initialized, and the automatic power off timer incorporated in the control unit 10 is set. When none of the switches 2, 3, 4 has been pressed for a predetermined time, for example, five minutes, the timer indicates a time-out (step 4). At step 5, the power supply is turned off in order to prevent exhaustion of the battery from occurring when the instrument is neglected.

At step 2, it is judged whether the Set switch 2 has been pressed. If the power supply is turned on, control is passed to step 3. A body fat occupancy ratio and an amount of body fat are measured according to a known procedure, and the results of measurement (performed by control unit 10) are displayed on the display unit 5. At step 4, the automatic power off timer is checked. If the timer does not indicate a time-out, control is returned to step 2 so that the results of measurement will be kept displayed at step 3. If the timer indicates a time-out, the power supply is turned off at step 5.

In the body fat display mode, if the Set switch 2 is turned on, judgment is made in the affirmative at step 2 and judgment is made in the negative at step 6. At step 7, the body fat re-measurement mode is established. When the re-measurement mode is established, data such as a sex of a measurer, an age thereof, a height thereof, and a weight thereof is entered in order to measure a body fat occupancy ratio and an amount of body fat according to a known procedure. The data is stored in the memory 14. Control is then passed to step 3 of measuring and displaying the body fat occupancy ratio and amount of body fat. In the remeasurement mode, if the Set switch 2 is turned on, judgment is made in the affirmative at step 6. Control is then passed to step 8. At step 8, judgment is made in the negative. Control is then passed to step 9 of measuring and displaying a blood pressure. For measuring a blood pressure, the electrodes A, B, C, and D are used to detect an electrocardiographic wave. The photoelectric sensor 6 is touched with a fingertip in order to detect a pulse wave. A blood pressure is measured through calculation based on a time lag of the pulse wave from the electrocardiographic wave.

When the Set switch 2 is turned on in the blood pressure measurement mode, judgment is made in the affirmative at step 8. Control is passed to step 10. The photoelectric sensor 6 is touched with a fingertip in order to detect a change in blood flow, whereby a pulse rate is measured in a known manner. The results of measurement are then indicated.

According to the present embodiment, photoelectric sensor 6 is used to measure a pulse rate. Alternatively, instead of employing photoelectric sensor 6, a pulse wave may be detected based on a change in a bioelectrical impedance occurring between the electrodes. In this case, a measurer having an injured finger can measure his/her pulse rate or the like.

Figure 5:
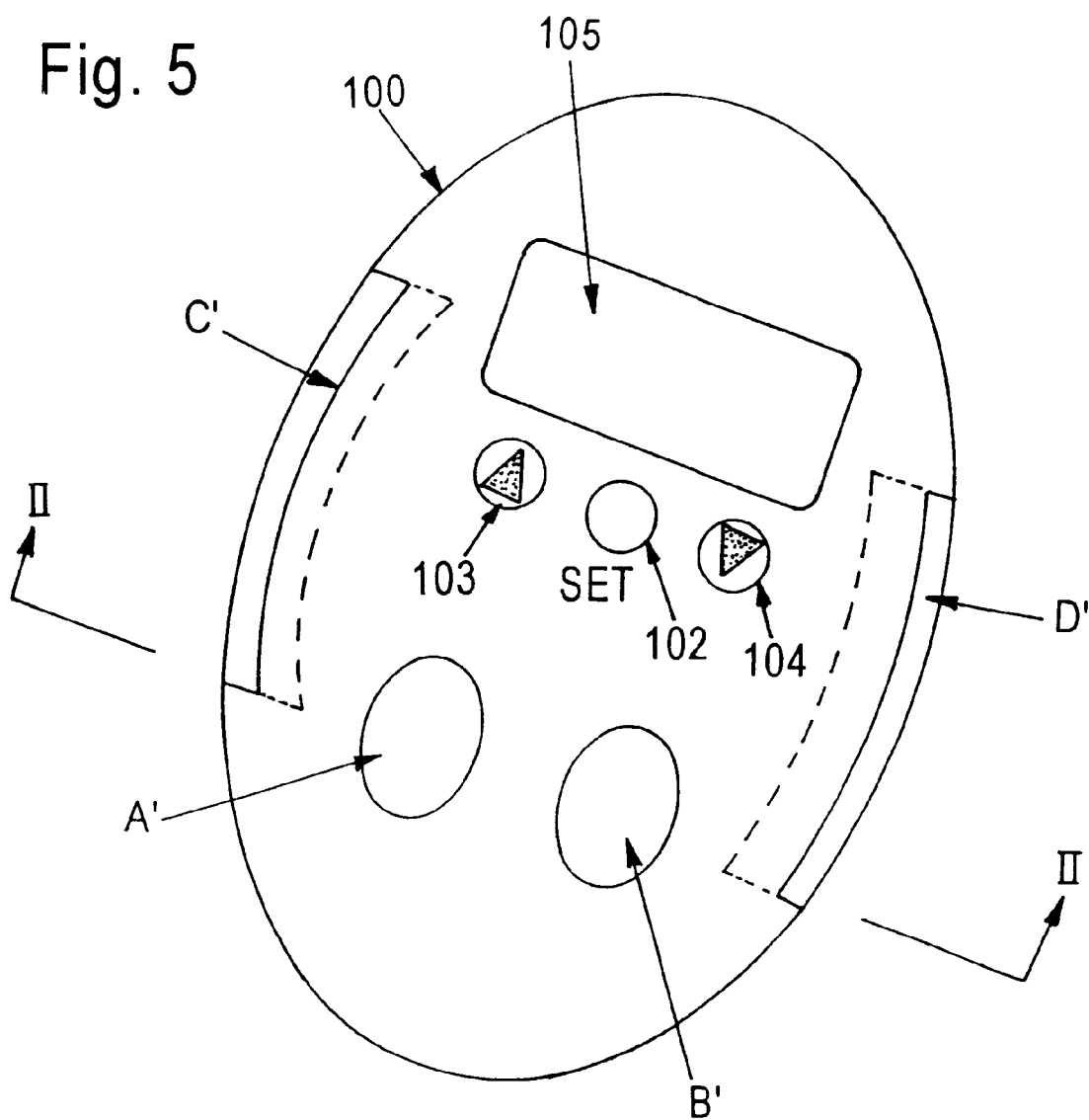
FIG. 5 illustrates a portable bioelectrical impedance measuring instrument in accordance with a second embodiment of the present invention.
Figure 6:
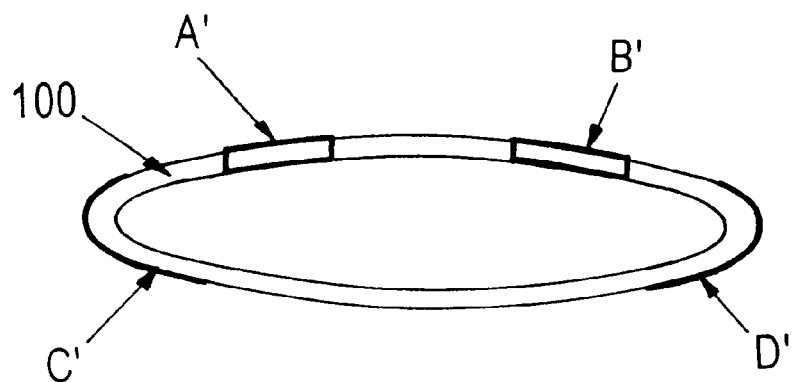
FIG. 6 is a cross sectional view taken through line II—II of the measuring instrument shown in FIG. 5.

Referring to FIG. 5 and FIG. 6, the second embodiment of the present invention will be described below.

The embodiment shown in FIGS. 5 and 6 differs from the first embodiment shown in FIG. 1 in that while the pair of electrodes C and D are on the back of main body 1 in the embodiment of FIG. 1, in the embodiment of FIGS. 5 and 6, electrodes C' and D' are located on opposing sides of a main body 100. Furthermore, photoelectric sensor 6 is excluded. The other components of the embodiment of FIGS. 5 and 6 are identical to those of the first embodiment. Reference numerals employed in FIGS. 5 and 6 are one hundred larger than those employed in the first embodiment. The same letters as those employed in the first embodiment are used in FIGS. 5 and 6 with a dash appended thereto.

The actions to be performed by the apparatus of the second embodiment are identical to those performed by the apparatus of the first embodiment except that the blood pressure measurement mode is not included.

Similarly to the first embodiment, the photoelectric sensor may be included.

According to the second embodiment, the electrodes C' and D' to be touched with the palm of a hand are located on opposing sides of a main body 100. The main body 100 is held firmly in the palm of a hand. The main body 100 is therefore less prone to being dropped compared with that of the first embodiment. Moreover, the electrodes C' and D' are touched more reliably. This leads to stable measurement.

Figure 7:
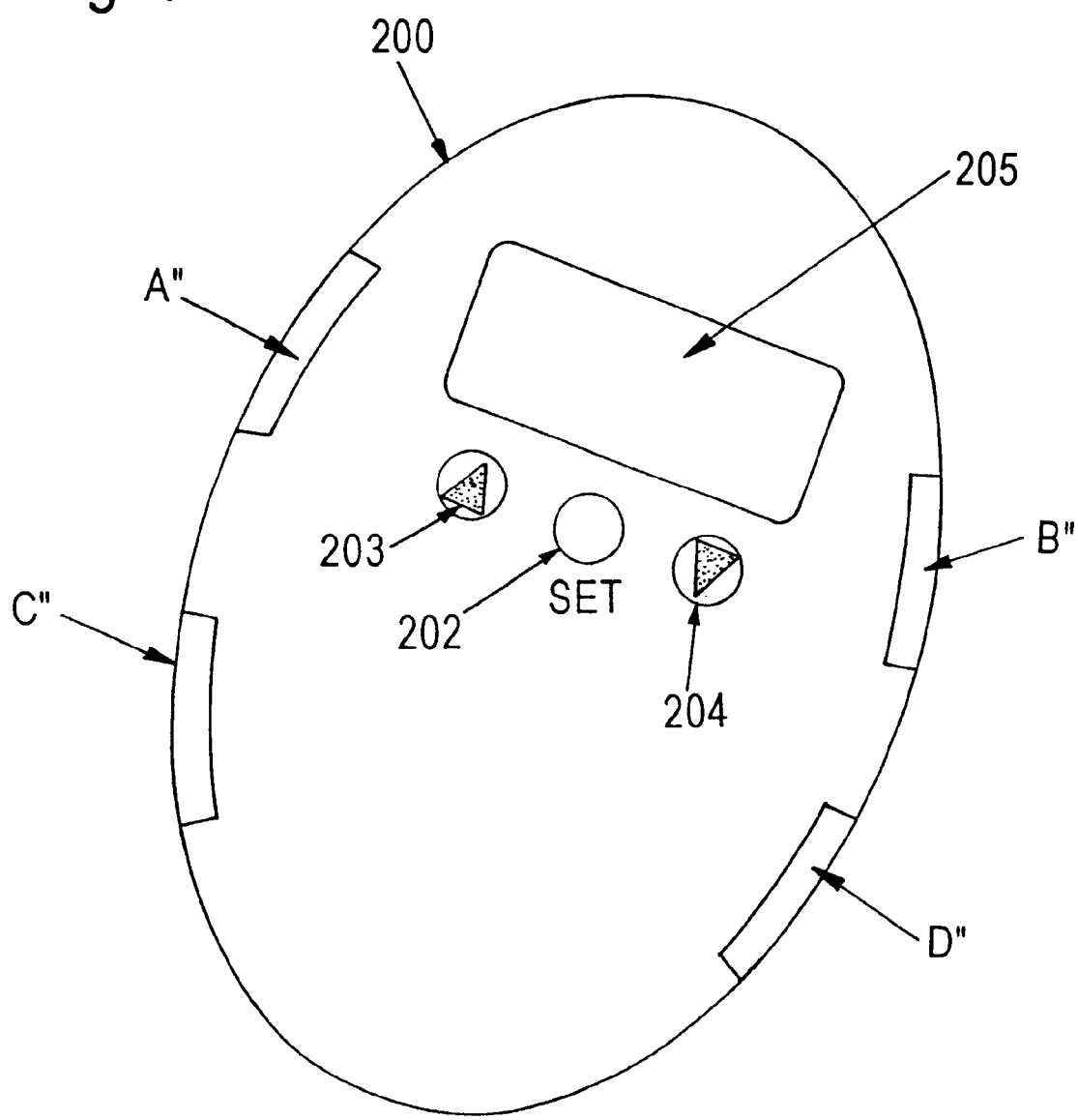
FIG. 7 illustrates a portable bioelectrical impedance measuring instrument in accordance with a third embodiment of the present invention.

Referring to FIG. 7, the third embodiment of the present invention will be described. The present embodiment has four electrodes A", B", C", and D" formed, like the electrodes C' and D' shown in FIG. 6, on opposing sides of a main body 200 so that the electrodes will extend from the face of the main body to the back thereof. The main body 200 is held in the palm of the right or left hand with both sides thereof clamped. Thus, a user having an injured finger can achieve measurement.

The other components of the third embodiment are identical to those shown in FIG. 1 and FIG. 5. Reference numerals employed in FIG. 7 are two hundred larger than those employed in the first embodiment.

In the aforesaid embodiments, the main body is shaped nearly like a circular cylinder. However, the shape is not limited to any specific shape as long as the main body can be held in the palm of a hand. The shape may be an elliptic cylinder or parallelepiped.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A portable bioelectrical impedance measuring instrument comprising:
   a main body, substantially parallelepiped shaped and comprising an insulating material, said main body comprising a back side, at least a portion of the back side having a curved shape;
   a first pair of electrodes, spaced apart from each other, on a face of said main body;
   a second pair of electrodes, spaced apart from each other, on the curved portion of the back side of the main body opposite the face;
   a display unit on the face of said main body; and
   an operator unit on the face of said main body;

wherein the first and second pairs of electrodes are disposed such that, when a user holds the main body with one hand, a palm of the one hand can contact the second pair of electrodes and the user's other hand can contact the first pair of electrodes.

2. A portable bioelectrical impedance measuring instrument comprising:

a main body, substantially parallelepiped shaped and comprising an insulating material, said main body comprising a face, a back side, and opposing sides connecting the face and the back side, at least a portion of the opposing sides having a curved shape;

a first pair of electrodes, spaced apart from each other, on a face of said main body;

a second pair of electrodes spaced apart from each other, on curved portions of opposing sides of the main body;

a display unit on the face of said main body; and an operator unit on the face of said main body;

wherein the first and second pairs of electrodes are disposed such that, when a user holds the main body with one hand, a palm of the one hand can contact the second pair of electrodes and the user's other hand can contact the first pair of electrodes.

3. A portable bioelectrical impedance measuring instrument comprising:

a main body, substantially parallelepiped shaped and comprising an insulating material, the main body having a face, a back surface opposite the face, and a pair of opposing side surfaces at least a portion of said opposing side surfaces being curved;

two pairs of electrodes, spaced apart from each other, on the curved portions of the pair of opposing sides of said main body;

a display unit on the face of said main body; and an operator unit on the face of said main body;

wherein the two pairs of electrodes are disposed such that a user can contact the electrodes on one of the opposing sides of the main body with only the palm of one hand while simultaneously contacting the electrodes on the other opposing side of the main body with only the palm of the other hand.

4. A portable bioelectrical impedance measuring instrument according to any of claims 1 to 3, wherein said portable bioelectrical impedance measuring instrument is for measuring a body fat occupancy ratio.

5. A portable bioelectrical impedance measuring instrument according to claim 1, 2, or 3, wherein said portable bioelectrical impedance measuring instrument is for measuring a pulse rate.

6. A portable bioelectrical impedance measuring instrument according to claim 1, 2, or 3, wherein said portable bioelectrical impedance measuring instrument is for measuring a blood pressure.

7. A portable bioelectrical impedance measuring instrument comprising:

a main body, substantially parallelepiped shaped and comprising an insulating material, the main body having a face, a back surface opposite the face, and a pair of opposing side surfaces;

two pairs of electrodes, spaced apart from each other, on the pair of opposing sides of said main body;

a display unit on the face of said main body;

an operator unit on the face of said main body; and a reflective photoelectric detecting means in said main body, wherein the two pairs of electrodes are disposed such that a user can contact the electrodes on one of the opposing sides of the main body with only the palm of one hand while simultaneously contacting the electrodes on the other opposing side of the main body with only the palm of the other hand.

8. A portable bioelectrical impedance measuring instrument comprising:

a main body having a back side defining a curved outer surface over at least a portion thereof;

a first pair of electrodes on a face of the main body;

a second pair of electrodes on the curved portion of a back side of the main body opposite the face; and an operator unit on the face;

wherein the first and second pairs of electrodes are disposed such that, when a user holds the main body with one hand, a palm of the one hand can contact the second pair of electrodes and the user's other hand can contact the first pair of electrodes.

9. The instrument of claim 8, wherein the main body is substantially shaped as a parallelepiped, cylinder or elliptic cylinder.

10. The instrument of claim 8, wherein the main body comprises an insulating material.

11. The instrument of claim 8, further comprising a processor for calculating a body fat occupancy ratio or a pulse rate based on signals from the electrodes.

12. The instrument of claim 11, wherein the second pair of electrodes is located such that both electrodes of the second pair can simultaneously contact a palm of a user when the user holds the instrument in one of the user's hands.

13. The instrument of claim 8, further comprising a display unit on the face of the main body.

14. The instrument of claim 8, wherein the operator unit comprises a plurality of electrical switches.

15. A portable bioelectrical impedance measuring instrument comprising:

a main body, substantially parallelepiped shaped and comprising an insulating material;

a first pair of electrodes, spaced apart from each other, on a face of said main body; a second pair of electrodes, spaced apart from each other, on a back side of the main body opposite the face;

a display unit on the face of said main body;

an operator unit on the face of said main body; and a reflective photoelectric detecting means in said main body, wherein the first and second pairs of electrodes are disposed such that, when a user holds the main body with one hand, a palm of the one hand can contact the second pair of electrodes and the user's other hand can contact the first pair of electrodes.

16. A portable bioelectrical impedance measuring instrument comprising:

a main body;

a first pair of electrodes on a face of the main body;

a second pair of electrodes on a back side of the main body opposite the face;

an operator unit on the face; and a reflective photoelectric detector on the face of the main body, wherein the first and second pairs of electrodes are disposed such that, when a user holds the main body with one hand, a palm of the one hand can contact the second pair of electrodes and the user's other hand can contact the first pair of electrodes.

17. The instrument of claim 16, further comprising a processor for calculating a blood pressure based on signals from the electrodes and the photoelectric detector.

18. The instrument of claim 16, further comprising a processor for calculating a pulse rate based on a signal from the photoelectric detector.

19. A portable bioelectrical impedance measuring instrument comprising:
   a main body having a face, a back surface opposite the face, and opposing side surfaces connecting the face to the back surface, at least a portion of said back surface and said opposing side surfaces being curved,
   a first pair of electrodes on a face of the main body;
   a second pair of electrodes on curved portions of opposing sides of the main body; and
   an operator unit on the face;
   wherein the first and second pairs of electrodes are disposed such that, when a user holds the main body with one hand, a palm of the one hand can contact the second pair of electrodes and the user's other hand can contact the first pair of electrodes.

20. The instrument of claim 19, wherein the main body is substantially shaped as a parallelepiped, cylinder or elliptic cylinder.

21. The instrument of claim 19, wherein the main body comprises an insulating material.

22. The instrument of claim 21, wherein the electrodes of each of the first and second pairs of electrodes are spaced apart from each other.

23. The instrument of claim 22, wherein the second pair of electrodes is located such that both electrodes of the second pair can simultaneously contact a palm of a user when the user holds the instrument in one of the user's hands.

24. The instrument of claim 23, wherein each of the electrodes of the second pair of electrodes extends onto the face of the main body.

25. The instrument of claim 23, wherein each of the electrodes of the second pair of electrodes extends onto a back side of the main body opposite the face.

26. The instrument of claim 19, further comprising a display unit on the face of the main body.

27. The instrument of claim 19, wherein the operator unit comprises a plurality of electrical switches.

28. The instrument of claim 19, further comprising a processor for calculating a body fat occupancy ratio or a pulse rate based on signals from the electrodes.

29. A portable bioelectrical impedance measuring instrument comprising:
   a main body;
   a first pair of electrodes on a face of the main body;
   a second pair of electrodes on a back side of the main body opposite the face;
   an operator unit on the face; and
   a reflective photoelectric detector on the face of the main body,
   wherein the first and second pairs of electrodes are disposed such that, when a user holds the main body with one hand, a palm of the one hand can contact the second pair of electrodes and the user's other hand can contact the first pair of electrodes.

30. The instrument of claim 29, further comprising a processor for calculating a blood pressure based on signals from the electrodes and the photoelectric detector.

31. The instrument of claim 29, further comprising a processor for calculating a pulse rate based on a signal from the photoelectric detector.

32. A portable bioelectrical impedance measuring instrument comprising:
   a main body having a face, a back surface opposite the face, at least a portion of said back surface being curved, and a pair of opposing side surfaces, at least a portion of said opposing sides being curved;
   two pairs of electrodes on the curved portions of said pair of opposing sides of the main body; and
   an operator unit on the face of the main body;
   wherein the two pairs of electrodes are disposed on curved portions of opposing sides of the main body to extend from the face of the main body to a curved portion of the back surface opposite the face such that a user can contact the electrodes on one of the opposing sides of the main body with only the palm of one hand while simultaneously contacting the electrodes on the other opposing side of the main body with only the palm of the other hand.

33. The instrument of claim 32, wherein the main body is substantially shaped as a parallelepiped, cylinder or elliptic cylinder.

34. The instrument of claim 32, wherein the main body comprises an insulating material.

35. The instrument of claim 34, wherein the electrodes of each of the two pairs of electrodes are spaced apart from each other.

36. The instrument of claim 35, wherein the pairs of electrodes are located such that all the electrodes can simultaneously contact a palm of a user when the user holds the instrument in one of the user's hands.

37. The instrument of claim 36, wherein each of the electrodes of the pairs of electrodes extends onto the face of the main body.

38. The instrument of claim 36, wherein each of the electrodes of the pairs of electrodes extends onto a back side of the main body opposite the face.

39. The instrument of claim 32, further comprising a display unit on the face of the main body.

40. The instrument of claim 32, wherein the operator unit comprises a plurality of electrical switches.

41. The instrument of claim 32, further comprising a processor for calculating a body fat occupancy ratio or a pulse rate based on signals from the electrodes.

42. A portable bioelectrical impedance measuring instrument comprising:
   a main body, substantially parallelepiped shaped and comprising an insulating material;
   a first pair of electrodes, spaced apart from each other, on a face of said main body;
   a second pair of electrodes spaced apart from each other, on opposing sides of the main body;
   a display unit on the face of said main body;
   an operator unit on the face of said main body; and
   a reflective photoelectric detecting means in said main body,
   wherein the first and second pairs of electrodes are disposed such that, when a user holds the main body with one hand, a palm of the one hand can contact the second pair of electrodes and the user's other hand can contact the first pair of electrodes.

43. A method of measuring bioelectrical impedance using a handheld bioelectrical impedance measuring instrument comprising:

placing a handheld bioelectrical impedance measuring instrument comprising a main body having a front surface, a back surface, at least a portion of which is curved, and side surfaces, said main body bearing a first pair of electrodes on the front surface and bearing a second pair of electrodes on the curved portion of the back surface in the palm of a user with the back surface facing the user's palm and with the second pair of electrodes in contact with the user's palm;

touching the first pair of electrodes with an opposite hand to measure an impedance between the first pair of electrodes and the second pair of electrodes.

44. A method of measuring bioelectrical impedance using a handheld bioelectrical impedance measuring instrument according to claim 43, wherein said step of touching the first pair of electrodes with an opposite hand comprises touching said first pair of electrodes with fingers of the opposite hand.

* * * * *